United States Patent

Milner

Patent Number: 5,214,161
Date of Patent: May 25, 1993

[54] PREPARATION OF POLYCYCLIC DYES

[75] Inventor: David J. Milner, Whitefield, England

[73] Assignee: Imperial Chemical Industries PLC, London, England

[21] Appl. No.: 898,833

[22] Filed: Jun. 15, 1992

[30] Foreign Application Priority Data

Jun. 14, 1991 [GB] United Kingdom ............. 9112831.4

[51] Int. Cl.$^5$ ............................................. C07D 307/77
[52] U.S. Cl. ........................................ 549/299; 560/60
[58] Field of Search .......................................... 549/299

[56] References Cited

U.S. PATENT DOCUMENTS 3,549,699 12/1970 Simon .................................. 562/840

FOREIGN PATENT DOCUMENTS

| 0033583 | 8/1981 | European Pat. Off. . |
| 0252406 | 1/1988 | European Pat. Off. . |
| 0371223 | 6/1990 | European Pat. Off. . |
| 0363034 | 11/1990 | European Pat. Off. . |
| 2103231 | 2/1983 | United Kingdom . |

Primary Examiner—Bernard Dentz
Attorney, Agent, or Firm—Cushman, Darby & Cushman

[57] ABSTRACT

A process for the preparation of a polycyclic dye of the Formula (1):

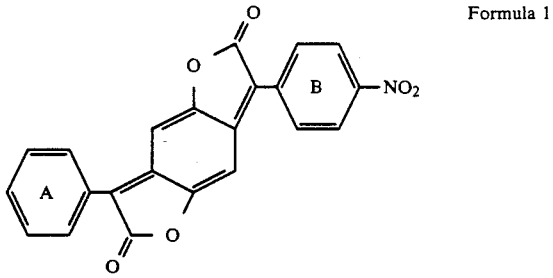

Formula 1 by reacting a ketal ester of the Formula (2):

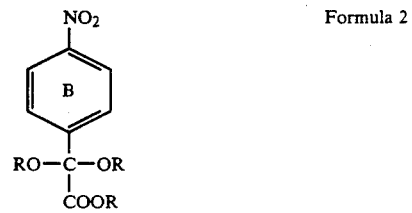

Formula 2 with a benzofuranone of the Formula (3):

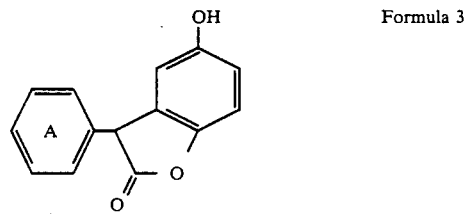

Formula 3 wherein:
  Ring A is unsubstituted or is substituted by from one to three groups;
  Ring B is unsubstituted, apart from the nitro group, or is substituted by one or two additional groups;
  each R is independently alkyl.

The polycyclic dyes described are useful for the coloration of synthetic textile materials especially polyesters.

1 Claim, No Drawings

PREPARATION OF POLYCYCLIC DYES

PREPARATION OF POLYCYCLIC DYES

This invention relates to a process for the preparation of certain polycyclic dyes, to certain novel polycyclic dyes and to novel intermediates used in the process.

According to the present invention there is provided a process for the preparation of a polycyclic dye of the Formula (1):

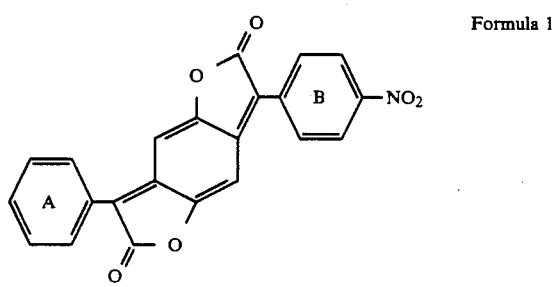

Formula 1 by reacting a ketal ester of the Formula (2):

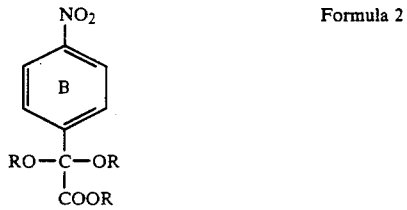

Formula 2 with a benzofuranone of the Formula (3):

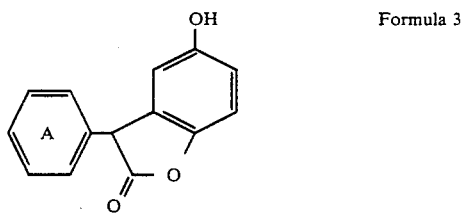

Formula 3 wherein:

Ring A is unsubstituted or is substituted by from one to three groups;

Ring B is unsubstituted, apart from the nitro group, or is substituted by one or two additional groups;

each R is independently alkyl.

Where Ring A carries substitutents these are preferably in the 4-position, or in the 3- and 4-position, or in the 3-, 4- and 5-positions.

Where Ring B carries substitutents, in addition to the nitro group, these are preferably in the 3-position or in both the 3- and 5-positions.

Suitable substituent groups for Ring A may be independently selected from —NO$_2$; —OH; —CF$_3$; halogen preferably —F, —Cl or —Br; —CN; —COOR$^1$ in which R$^1$ is —H or C$_{1-6}$-alkyl; —NR$^2$R$^3$ in which R$^2$ and R$^3$ are each independently —H, C$_{1-6}$-alkyl or C$_{1-6}$-alkyl substituted by —OH, —CN or halogen; —NHCOR$^4$; OR$^4$; —OR$^4$OR$^5$; —OR$^4$OR$^5$; —OR$^4$OR$^5$OR$^6$; —OR$^4$COOR$^5$; —OR$^4$COOR$^5$OR$^6$; —OR$^4$OCOR$^5$; and —OR$^4$OCOPh in which R$^4$, R$^5$ and R$^6$ are each independently C$_{1-6}$-alkyl, preferably C$_{1-4}$-alkyl.

Suitable substituent groups for Ring B may be independently selected from any of the groups described above for Ring A.

The alkyl groups represented by R may be either straight or branched chain alkyl groups. The alkyl groups represented by R may be substituted by any group which does not interfere in the reaction. The alkyl groups represented by R are preferably C$_{1-6}$-alkyl, more preferably C$_1$-alkyl and especially preferably methyl or ethyl.

In the compounds of Formula (2) the alkyl groups represented by R in the group:

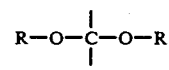

may be fused to form an alkylene group, X, and thus a cyclic diether group:

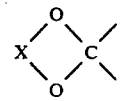

—X— is preferably C$_{1-8}$-alkylene, more preferably C$_{1-6}$-alkylene and especially —CH$_2$—, —CH$_2$CH$_2$—, —CH$_2$CH(CH$_3$)CH$_2$— and —CH$_2$C(CH$_3$)$_2$CH$_2$—.

The present process may be performed by stirring the reactants in a liquid medium, preferably in an acidic medium, more preferably in an organic acid and especially preferably in methane sulphonic acid, ethanoic acid, propanoic acid or butanoic acid.

The process is preferably carried out at a temperature from 0° C. to 100° C., more preferably from 10° C. to 50° C. and especially preferably from 15° C. to 30° C.

When the reaction is substantially complete, as judged by disappearance of starting materials using a technique such as thin layer chromatography, the product may be isolated in any convenient manner. For example the product may be precipitated from the reaction mixture, by addition of water, and filtered off, washed with water and dried.

According to a further feature of the present invention there is provided a compound of Formula (2) wherein R and Ring B are as hereinbefore defined.

Compounds of the Formula (2) may be prepared either by reaction of (a) a nitrophenylglyoxylic acid of Formula (5) or (b) a nitrobenzoylformate ester of Formula (6) with an alcohol, ROH, preferably containing gaseous hydrogen chloride and preferably under dehydrating conditions according to the following scheme:

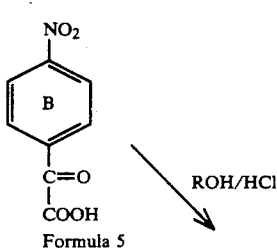

Formula 5

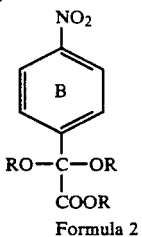

Formula 2

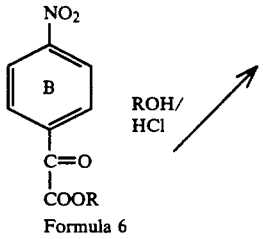

Formula 6 wherein: Ring B and R are as hereinbefore defined.

Dehydrating conditions can be provided by the presence of a dehydrating agent such as triethylorthoformate or by performing the reaction under azeotroping conditions in the presence of an azeotroping liquid such as toluene. These reactions may be conveniently carried out at temperatures from 0° C. to 100° C., preferably at from 15° C. to 60° C. and more preferably at 15° to 30° C. optionally in an autoclave at pressures from 0.1 to 10 bar preferably at 0.1 to 5 bar. The alcohol used in the preparation of the compound of Formula (2) is preferably a straight or branched chain $C_{1-6}$-alkyl alcohol, more preferably straigtht or branched chain $C_{1-4}$-alkyl alcohol and especially preferably methanol, ethanol, isopropanol or n-butanol. A mixture of different alcohols may be used to prepare compounds of Formula (2) where the alkyl groups represented by R are different. Cyclic ketal esters wherein two alkyl groups represented by R are fused to form a cyclic diether group may be prepared by using an appropriate diol, $X(OH)_2$, wherein X is as hereinbefore defined as the alcohol either alone or in conjunction with a monofunctional alkanol, ROH. Examples of suitable diols include ethan-1,2-diol or 2,2-dimethylpropan-1,3-diol. The compounds of Formula (2) may be conveniently isolated from the reaction mixture by removing excess alcohol, hydrogen chloride and triethylorthoformate under vacuum.

Compounds of the Formula (3) may be conveniently prepared by reaction of a dihydroxybenzene or hydroquinone with a mandelic acid derivative in 70% sulphuric acid or in acetic acid/sulphuric acid mixtures at elevated temperatures, the product may be recovered by filtration after diluting the reaction mixture with water. EP 0033583 provides examples of such preparations.

According to a further feature of the present invention there is provided a compound of Formula (1) wherein Ring A is as hereinbefore described and Ring B carries at least one substituent in addition to the nitro group selected from those described as suitable for Ring A above. The substituents in Ring B, in addition to the nitro group, are preferably in the 3-position or in both the 3- and 5-positions. The substituent in Ring B, at the 3- or 3- and 5-positions, is preferably $C_{1-6}$-alkyl, more preferably $C_{1-4}$-alkyl and especially methyl, ethyl, isopropyl or isobutyl.

According to a further feature of the present invention there is provided a process for the preparation of a polycyclic dye of Formula (4):

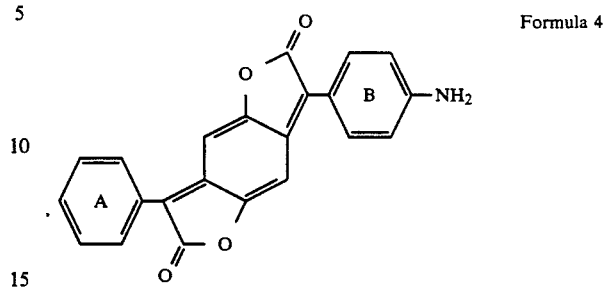

Formula 4 wherein: Ring A and Ring B are as hereinbefore defined by reduction of a polycyclic dye of Formula (1).

The compound of Formula (1) may be reduced to a compound of Formula (4) by any of the known methods for reducing a nitro group to an amino group which does not also adversely affect the rest of the molecule. Preferred methods include:

(i) dissolving or dispersing the compound of Formula (1) in a liquid medium, preferably in an ether, more preferably in an aromatic-aliphatic ether such as anisole or phenetole or in an aromatic-aromatic ether such as diphenylether, adding a catalyst preferably a precious metal such as palladium or platinum carried on a support such as carbon or aluminium oxide and stirring at a temperature from 0° C. to 100° C., preferably at 15° C. to 50° C., under from 0.1 to 10 bar, preferably from 1 to 4 bar hydrogen pressure; or (ii) dissolving or dispersing the compound of Formula (1) in a liquid medium, preferably in an alcohol such as methanol, ethanol, isopropanol, n-propanol or n-butanol, adding an alkali metal borohydride such as sodium or potassium borohydride and a metal chloride such as tin (II) chloride or copper chloride and stirring at a temperature from 15° C. to 60° C.

The compound of Formula (4) may be conveniently isolated by filtration followed by distillation, optionally under vacuum, to remove the liquid medium. The compound of Formula (4) may be conveniently purified by crystallisation from a solvent such as 1,2-dichlorobenzene or by column chromatography by elution from a silica column with a solvent such as dichloromethane.

According to a further feature of the present invention there is provided a process for the preparation of compounds of the Formula (2) wherein Ring B carries, in addition to the 4-nitro group, an alkyl or aralkyl group in the 3-position by reaction of an alkyl or aralkyl Grignard reagent with a compound of the Formula (2) in which the 3-position is free of substituents wherein R and Ring B are as hereinbefore defined. The alkyl group is preferably $C_{1-6}$-alkyl, more preferably $C_{1-4}$-alkyl, and especially preferably methyl, ethyl, isopropyl or isobutyl. The aralkyl group is preferably aryl-$C_{2-6}$-alkyl, more preferably aryl-$C_{2-4}$-alkyl and especially phenyl-$C_{2-4}$-alkyl, such as phenyl-$(CH_2)_2$. The halogen atom of the Grignard Reagent is preferably selected from —I, —Br and —Cl. This process may be conveniently carried out at a temperature from —50° to —5° C., preferably from —35° to —5° C., more preferably from —20° to —10° C. and especially preferably at —15° C. The process may be carried out in any liquid medium which does not react with either the compound of Formula (2) or the Grignard reagent. The liquid medium is preferably an inert solvent, more preferably an ether and especially preferably tetrahydrofuran or diethyl ether. When the reaction is substantially complete the product may be isolated by pouring the reaction mixture into water and extracting with a suitable water-immiscible liquid such as dichloromethane. Evaporation of the liquid extractant leaves the product.

The dyes of Formula (1) and Formula (4) are useful for the coloration of synthetic textile materials and especially polyesters.

The invention is further illustrated by the following Examples in which all parts and percentages are by weight.

EXAMPLE 1

Preparation of 3-phenyl-7-(4-nitrophenyl)-2,6-dioxo-2,6-dihydrobenzo[1:2-b, 4:5-b']difuran (i) 4-nitrophenylglyoxylic acid (2.27 parts) in methanol (100 parts) containing triethylorthoformate (10.6 parts) was saturated with gaseous hydrogen chloride and was allowed to stand at ambient temperature for 4 days. The methanol, triethylorthoformate and hydrogen chloride were removed under vacuum to leave a residue (2.4 parts, 81%) of methyl 2,2-dimethoxy-2-(4-nitrophenyl)ethanoate identified by its mass spectrum and nmr spectrum.

(ii) Methyl 2,2-dimethoxy-2-(4-nitrophenyl)ethanoate (0.12 parts) and 5-hydroxy-2-oxo-3-phenyl-2,3-dihydrobenzofuran (0.1 part) were stirred in methane sulphonic acid (5 parts) at ambient temperature for 2 days. Water (50 parts) was added to the reaction mixture and the precipitated solid was filtered off, washed acid free and dried to give 3-phenyl-7-(4-nitropheny)-2,6-dioxo-2,6-dihydrobenzo[1:2-b, 4:5-b'] difuran (0.18 parts, 73%); λ max in dicholomethane=462 nm.

EXAMPLE 2

Preparation of 3-phenyl-7-(4-aminophenyl)-2,6-dioxo-2,6-dihydrobenzo[1:2-b, 4:5-b']difuran 3-Phenyl-7-(4-nitrophenyl)-2,6-dioxo-2,6-dihydrobenzo[1:2-b, 5:5-b']difuran (0.05 parts) was dissolved in anisole (200 parts) and 3% palladium on carbon catalyst (0.2 parts) was added. The mixture was stirred at 25° C. under 80 psig hydrogen pressure for 4 hours. The reaction mixture was filtered to remove the catalyst and the anisole was removed by distillation under vacuum to leave 3-phenyl-7-(4-aminophenyl)-2,6-dioxo-2,6-dihydrobenzo[1:2-b, 4:5-b']difuran (0.023 parts, 50%); λ max in acetonitrile=566 nm.

EXAMPLE 3

Preparation of 3-phenyl-7-(3-isobutyl-4-nitrophenyl)-2,6-dioxo-2,6-dihydrobenzo[1:2-b, 4:5-b']difuran (i) Methyl 2,2-dimethoxy-2-(4-nitrophenyl)ethanoate (2.0 parts) was dissolved in tetrahydrofuran (100 parts) and the solution was stirred at −15° C. whilst a 2 mol.dm$^{-3}$ solution of isobutylmagnesium chloride in diethylether (3 parts) was added. After stirring the reaction mixture for 30 minutes further isobutylmagnesium chloride in diethyl ether (3 parts) was added and the reaction mixture was stirred for a further 60 minutes before adding dichlorodicyanobenzoquinone (3 parts). The reaction mixture was stirred for 16 hours and allowed to warm to ambient temperature. Water (300 parts) was added to the reaction mixture and the resultant mixture was extracted with dichloromethane (3 x 150 parts). The extracts were combined, diluted with dichloromethane (50 parts) and a portion was analysed by gas chromatography-mass spectrometry. Methyl 2,2-dimethoxy-2-(3-isobutyl-4-nitrophenyl)ethanoate was identified as the only volatile product by its mass spectrum (m/e 312, 252).

(ii) the dichloromethane solution of methyl 2,2-dimethoxy-2-(3-isobutyl-4-nitrophenyl)ethanoate (250 parts) from (i) above was evaporated under vacuum to leave a residue (1.93 parts). The residue was stirred with methanesulphonic acid (10 parts) and 5-hydroxy-2-oxo-3-phenyl-2,3-dihydrobenzofuran (2 parts) at ambient temperature for 3 days. The reaction mixture was added to water (200 parts) and the precipitated solid was collected by filtration and dried. The dry solid was dissolved in hot 1,2-dichlorobenzene (50 parts) and the resultant solution was filtered, before removing the solvent under vacuum to leave a residue (1.1 parts). The residue was further purified by column chromatography by elution with dichloromethane from silica. Combination of eluates and evaporation of dichloromethane gave 3-phenyl-7-(3-isobutyl-4-nitrophenyl)-2,6-dioxo-2,6-dihydro[1:2-b, 4;5-b']difuran (0.83 parts), m/e=441, λ max=461 nm.

EXAMPLE 4

Preparation of 3-phenyl-7-(3-isobutyl-4-aminophenyl)-2,6-dioxo-2,6-dihydrobenzo[1:2-b, 4:5-b']difuran 3-Phenyl-7-(3-isobutyl-4-nitrophenyl)-2,6-dioxo-2,6-dihydrobenzo[1:2-b, 4:5-b']difuran (0.72 parts) and hydrated stannous chloride (2.7 parts) were stirred in ethanol (300 parts) at 50° C. A solution of sodium borohydride (0.11 parts) in ethanol (76 parts) was added in portions to the reaction mixture before each portion of sodium borohydride solution was added. Sufficient stannous chloride was added to maintain the tin:boron ratio.

The reaction mixture was poured onto a mixture of ice and water (500 parts) and the ethanol was removed by distillation. The precipitated solid was collected by filtration. The solid was purified by column chromatography by elution with dichloromethane from silica. Combination of eluates and evaporation of dichloromethane gave 3-phenyl-7-(3-isobutyl-4-aminophenyl)-2,6-dioxo-2,6-dihydrobenzo[1:2-b, 4:5-b']difuran (0.32 parts), m/e=411, λ max=568 nm.

I claim:

1. A process for the preparation of a polycyclic dye of the Formula (1):

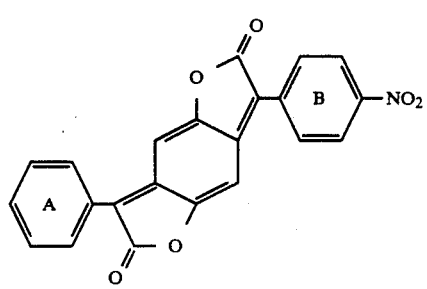

Formula 1 by reacting a ketal ester of the Formula (2):

with a benzofuranone of the Formula (3):
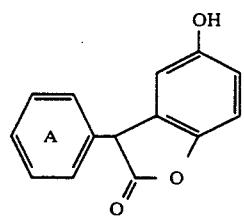
Formula 3
wherein:
Ring A is unsubstituted or is substituted by from one to three groups;
Ring B is unsubstituted, apart from the nitro group, or is substituted by one or two additional groups;
each R is independently alkyl.
* * * * *